United States Patent [19]

Malik et al.

[11] Patent Number: 5,643,757

[45] Date of Patent: Jul. 1, 1997

[54] **HIGH YIELD PRODUCTION OF HUMAN APOLIPOPROTEIN A1 IN *E. COLI*.**

[75] Inventors: Sohail Malik, Englewood Cliffs, N.J.; Florence Mahlberg, Suresnes, France; Sotirios Karathanasis, Grandview, N.Y.

[73] Assignee: American Cyanamid Company, Wayne, N.J.

[21] Appl. No.: 215,749

[22] Filed: Mar. 21, 1994

[51] Int. Cl.$^6$ .............................. C12N 15/70; C07K 1/22

[52] U.S. Cl. ................ 435/69.7; 435/69.6; 435/252.33; 435/320.1; 935/39; 530/413; 530/415

[58] Field of Search ........................ 435/69.6, 69.7, 435/252.33, 320.1; 935/39; 530/413, 415

[56] References Cited

U.S. PATENT DOCUMENTS

| | | | |
|---|---|---|---|
| 4,643,988 | 2/1987 | Segrest et al. | 514/12 |
| 4,943,527 | 7/1990 | Protter et al. | 435/69.6 |
| 5,128,318 | 7/1992 | Levine et al. | 514/2 |
| 5,278,189 | 1/1994 | Rath et al. | 514/561 |
| 5,284,933 | 2/1994 | Döbeli et al. | 530/409 |

OTHER PUBLICATIONS

Ausubel, F.M., et al., eds., Short Protocols in Molecular Biology, 2nd ed., John Wiley & Sons, New York, 1992, Figure 16.2.1, p. 16–7.
Breyer, R.M., et al., EMBO J. 9: 2679–2684 (1990).
Campbell, W.H., Plant Physiol. 99: 693–699 (1992).
Cheung, P. and Chan, L., Nucl. Acids Res. 11: 3703–3715 (1983).
Citovsky, V., et al., Proc. Nat. Acad. Sci. 86: 1193–1197 (1989).
Flegel, W.A., et al., Infection and Immunity 61: 5140–5146 (1993).
Hoffman, A. and Roeder, R.G., Nucl. Acids Res. 19: 6337–6338 (1991).
Karathanasis, S., et al., Proc. Natl. Acad. Sci. USA 80: 6147–6151 (1983).
Malik, et al., Proc. Natl. Acad. Sci. 88: 9553–9557 (1991).
Mallory, J.B., et al., J. Biol. Chem. 262: 4241–4247 (1987).
Studier, F.W., and Moffatt, B.A., J. Mol. Biol. 189: 113–130 (1986).

*Primary Examiner*—Stephen Walsh
*Attorney, Agent, or Firm*—Darby & Darby

[57] ABSTRACT

Apolipoprotein A1 is prepared in a T7 RNA polymerase/promoter bacterial expression system that optimizes yield and facilitates subsequent purification of the protein. Apolipoprotein A1 cDNA is cloned into an *Escherichia coli* plasmid containing a bacteriophage T7 RNA polymerase promoter such as a pT or pET plasmid; the recombinant plasmid is transferred to an *E. coli* strain containing inducible bacteriophage T7 RNA polymerase, e.g., a strain having the enzyme under lac control; T7 RNA polymerase is induced in the strain; and apolipoprotein A1 is isolated from the culture. Preferred embodiments tag the apolipoprotein with a sequence such as a stretch of histidines that facilitates purification subsequent to expression. An especially preferred embodiment employs a pET11d-6His plasmid and *E. coli* strain BL21(DE)pLysS that produces at least 1 mg protein per liter of culture, preferably up to 2 mg per liter, and the protein can be purified to homogeneity by one-step affinity chromatography on a nickel chelating resin.

15 Claims, No Drawings

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( i i ) MOLECULE TYPE:
        ( A ) DESCRIPTION: oligonucleotide ( v ) FRAGMENT TYPE: synthetic DNA ( i x ) FEATURE:
        ( D ) OTHER INFORMATION: primer used to prepare constructs ( x i ) SEQUENCE DESCRIPTION: SEQ ID NO:1:

```
AGCCGAGGAT CCTCACTGGG TGTTGAGCTT                    30
```

( 2 ) INFORMATION FOR SEQ ID NO:2:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( i i ) MOLECULE TYPE:
        ( A ) DESCRIPTION: oligonucleotide ( v ) FRAGMENT TYPE: synthetic DNA ( i x ) FEATURE:
        ( D ) OTHER INFORMATION: primer used to prepare constructs ( x i ) SEQUENCE DESCRIPTION: SEQ ID NO:2:

```
CTTTCGCATA TGGATGAACC CCCCCAGAGC                    30
```

HIGH YIELD PRODUCTION OF HUMAN APOLIPOPROTEIN A1 IN *E. COLI.*

TECHNICAL FIELD OF THE INVENTION

This invention relates to the production of pure, stable, mature and biologically active human apolipoprotein A1 in high yield using a bacterial expression system. The protein plays a role in various circulatory processes, including reverse cholesterol transport, atherosclerosis, restenosis, and septic shock.

BACKGROUND OF THE INVENTION

Epidemiological and genetic studies have implicated decreased plasma levels of high density lipoproteins (HDL) in the pathogenesis of atherosclerosis, whereas increased HDL levels have been correlated with protection against coronary heart disease and associated with longevity (Karathanasis, S., et al., *Proc. Natl. Acad. Sci. USA* 80: 6147–6151 (1983)). The molecular bases for these observations have not been elucidated, but it has been shown experimentally that HDL stimulates cholesterol efflux from cells and may in this manner act as a carrier for reverse cholesterol transport, i.e., the delivery of cholesterol from the peripheral tissues to the liver for disposal (ibid.). This mechanism could in part explain the inverse correlation observed between the size of total body cholesterol pools and plasma HDL levels, and between HDL levels and coronary heart disease. It also is possible that HDL might simply be a marker of a certain pattern of lipid transport and metabolism which confers protection against the development of atherosclerosis.

Apolipoprotein A1 (apoA1) is the major protein constituent of HDL. It is thought that, because of their involvement in cholesterol excretion, apoA1 and HDL are important in protection against coronary heart disease. Indeed, genetic deficiencies in apoA1 and HDL are associated with intracellular cholesterol accumulation and premature atherosclerosis.

ApoA1 is a relatively abundant (~1 to 1.5 mg/ml) plasma protein of known primary structure (see Karathanasis, et al., cited above, Cheung, P., and Chan, L., *Nucl. Acids Res.* 11: 3703–3715 (1983), and the references cited therein). ApoA1 has been shown to be a necessary component in mixtures with phospholipid for the successful removal of cholesterol from ascite cell membranes, and the protein is a potent activator/cofactor of lecithin:cholesterol acyltransferase, a plasma enzyme that catalyzes the conversion of cholesterol and phosphatidylcholine to cholesterol esters and lysophosphatidylcholine (ibid.).

ApoA1 appears to be synthesized predominantly in the liver and small intestine of mammals, but has been found in a variety of other tissues in the rooster (ibid.). The cDNA for human hepatic apoA1 has been cloned by different laboratories (Karathanasis, et al., and Cheung and Chan, cited above). The primary translation product of apoA1 mRNA is a preprotein that undergoes intra- and extracellular proteolytic processing to produce the major apoA1 isoprotein form observed in plasma. Deficiencies of apoA1 are associated with abnormalities in lipoprotein metabolism that result in low plasma HDL levels and may contribute to the development of premature atherosclerosis.

In addition to its imperfectly understood role in cholesterol transport and atherosclerosis, apoA1 appears to play a role in restenosis and septic shock, conditions involving circulatory disturbances. Restenosis is the narrowing or stricture of blood vessels, typically after angioplasty or surgical correction of the condition. Septic shock, associated with both gram-negative and gram-positive infections, is characterized by inadequate vasomotor tone resulting in profound hemodynamic disturbances involving a marked decrease in peripheral vascular resistance. Recently, purified apoA1 has been shown to prevent endotoxin-induced monokine release by human low- and high-density lipoproteins (Flegel, W. A., et al., *Infection and Immunity* 61: 5140–5146 (1993)).

Studies aimed at establishing the mode of action of apoA1, including its role in pathological processes and in lipid metabolism, and elucidation of its crystal structure, have been hampered by the lack of sufficiently large amounts of the protein. Isolations from plasma are arduous. The protein has been expressed in Chinese hamster ovary cells, but only about 30% yields of secreted protein have been achieved (Mallory, J. B., et al., *J. Biol. Chem.* 262: 4241–4247 (1987)). Attempts have been made to express the protein in bacteria as a β-galactosidase fusion protein, but the apoA-1 fusion product was found to be sensitive to degradation in culture (ibid.) The protein was expressed in *E. coli*, but the heterologous protein was unstable with a half-life of <10 minutes as determined by pulse-chase experiments (ibid.).

It would be desirable to have large quantities of apoA1 available at a reasonble cost.

SUMMARY OF THE INVENTION

It is an object of the invention to provide apolipoprotein A1 in high yield.

It is a further and more specific objective of the invention to provide pure, stable, mature and biologically active human apolipoprotein A1 in large quantities.

These and other objects are accomplished by the present invention, which provides a method for preparing apolipoprotein A1 in a bacterial expression system. Preferred embodiments yield at least 1, preferably 2 to 3, and most preferably as much as from about 5 to about 8, milligrams of protein per liter of culture.

In the practice of the method of the invention, apolipoprotein A1 is prepared in high yield using a T7 RNA polymerase/promoter system. The method comprises subcloning apolipoprotein A1 cDNA into an *Escherichia coli* plasmid containing a bacteriophage T7 RNA polymerase promoter such as a pT or a pET plasmid; transferring the recombinant plasmid to an *Escherichia coli* strain containing inducible bacteriophage T7 RNA polymerase such as a strain having a copy of the enzyme under lac control; inducing T7 RNA polymerase in the *Escherichia coli* strain; growing the strain in a culture for a time under conditions sufficient to produce expressed protein; and isolating apolipoprotein A1 from the culture.

In preferred embodiments, the *Escherichia coli* plasmid containing a bacteriophage T7 RNA polymerase promoter and a sequence for apoA1 also contains a DNA sequence encoding an amino acid sequence that facilitates purification of expressed proteins, e.g., a sequence for a cluster of negatively charged amino acids such as arginine, histidine, lysine, and mixtures thereof. Plasmids encoding 6 to 10 histidines are preferred. pET11d-6His is employed in one particularly preferred embodiment.

The recombinant plasmid is transferred to an *Escherichia coli* strain containing inducible bacteriophage T7 RNA polymerase, such as a strain having the enzyme under lac control, e.g. lacUV5 control. Strains that optimize expression are preferred; BL21(DE3) or HMS174(DE3) strains are typically employed. BL21(DE3)-pLysS is employed in one particularly preferreed embodiment. Expression is induced by the addition of isopropylthiogalactose to the culture.

After expression, the apolipoprotein A1 is isolated from the soluble fraction of the culture. In preferred embodments, the purification is carried out in one step using a metal affinity or chelating column such as a nickel (II)-nitrilotriacetic acid agarose or a metal chelating Sepharose® column charged with nickel (II).

DETAILED DESCRIPTION OF THE INVENTION

This invention is based upon the finding that human apolipoprotein A1 can be overproduced in very high yields in *Escherichia coli* using a T7 polymerase-promoter expression system. An apoA1 gene is introduced into a plasmid or other vector, the vector is introduced into living *E. coli* cells, and large amounts of apoA1 are produced under the direction of synthesis promoters.

In the practice of the method of the invention, a gene for apoA1 is cloned into a vector containing a promoter recognized by bacteriophage T7 RNA polymerase, and the gene is expressed by induction of T7 RNA polymerase in a modification of a method described by Studier, F. W., and Moffatt, B. A., *J. Mol. Biol.* 189: 113–130 (1986). The gene for T7 RNA polymerase is present on a second DNA construction that either permanently resides within the *E. coli* or is introduced into cells at the time of induction by infection with a specialized phage. The latter method is employed in one embodiment.

DNA encoding apoA1 for introduction into the bacterial vector may be natural products isolated from mammalian tissue using phenolic extraction followed by electrophoresis or the like standard procedures, or constructed cDNA prepared after screening genomic libraries. Cloned DNA is more readily available in quantity and is preferred. As mentioned above, cDNA for human hepatic apoA1 has been cloned by different laboratories (Karathanasis, et al., and Cheung and Chan, cited above). Any clone or subclone containing the complete sequence of mature apoA1, or a polymerase chain reaction (PCR) product synthesized from a clone, may be introduced into an *E. coli* vector for the bacterial expression of apoA1 according to the practice of the invention.

By "vector" is meant any self-replicating DNA molecule that can transfer a DNA segment between host cells, including plasmid cloning vectors. Any vector containing a bacteriophage T7 RNA polymerase promoter and having cloning sites may be employed, such as pT or pET plasmid cloning vectors described by Ausubel, F. M., et al., eds., *Short Protocols in Molecular Biology*, 2nd ed., John Wiley & Sons, New York, 1992, Figure 16.2.1, page 16-7; plasmids derived by inserting bacteriophage T7 DNA or T7 DNA plus lac, trp or tac DNA, or other DNA used as a marker or to promote transcription, into restriction sites such as BamHI on *E. coli* plasmids, e.g., pBR322 as described by Studier and Moffatt, cited above; or vectors commercially available from Novagen (Madison, Wis. 53711). pET vectors such as pET3, pET5, pET9, pET11, pET12, pET14, pET15, pET16, pET17, and pET19 to pET25 plasmids are preferred, especially the pET-11 series (pET11a–d), pET-15b, pET16b, pET-19b, the pET21 series, pET22b(+), the pET24 series, and pET25b(+). The pET11 series is particularly preferred. Plasmid pET11d is employed in one embodiment.

Vectors containing, in addition to the T7 promoter, a DNA sequence encoding a fusion product that facilitates purification of expressed proteins by cation or anion exchange, affinity, or immunoaffinity chromatography or the like are especially preferred. Examples include, but are not limited to, vectors encoding tags at the amino or carboxy terminus of the expressed protein such as a cluster of charged residues such as arginine, histidine, or lysine residues, or mixtures of these, which allows for rapid and inexpensive purification in one step by metal chelation chromatography. A typical tag is a stretch of 6 to 10 histidine residues. A plasmid pET11d-6His vector which encodes proteins expressed under T7 control as fusion products with a stretch of six histidine residues at the amino terminus is employed in one embodiment.

Once constructed, the expression vector containing the gene for apoA1 is introduced into an appropriate *E. coli* strain containing an inducible chromosomal copy of the T7 RNA polymerase gene, such as a strain having a copy of the enzyme under lac control. Transcription of the gene is induced by any means such as the addition of a chemical to, or physical manipulation of, the bacterial media. Typical hosts are lysogens of bacteriophage λDE3, which contains the polymerase gene under the control of an inducible lacUV5 promoter. In this system, the addition of isopropylthiogalactose (IPTG) to the culture induces the polymerase, which in turn transcribes the target DNA in the plasmid. A number of *E. coli* strains are commercially available for this purpose, including DH5α and lysogenic BL21(DE3) and HMS174(DE3) strains. BL21(DE3) strains are particularly preferred with pET plasmids; BL21(DE3)pLysS is employed in one embodiment.

After induction of T7 RNA polymerase, the *E. coli* strain is grown for a time under conditions sufficient to produce expressed protein in the culture. Any type of solidifed or liquid media that will support growth and reproduction of *E. coli* is useful in cultures for practicing the method of the invention, but liquid media is preferred to facilitate isolation of expressed proteins produced therein. Numerous suitable bacterial media are known to those skilled in the art, and an advantage of the invention is that *E. coli* is relatively easy and inexpensive to grow.

Typical media include both minimal and rich media. Minimal media include mixtures of magnesium sulfate and a carbon source, typically sugar or glycerol, with M9 medium containing disodium phosphate, monobasic potassium phosphate, ammonium chloride, sodium chloride and, optionally, calcium chloride, M63 medium containing ammonium sulfate, monobasic potassium phosphate, and ferrous sulfate, or A medium containing ammonium sulfate, monobasic potassium phosphate, dipotassium phosphate, and sodium citrate; thiamine, Casamino acids (Difco, Detroit, Mich. 48232-7038) or L amino acids, and antibiotics may be added, if required. Rich media include H medium containing tryptone and sodium chloride; λ-broth containing tryptone and sodium chloride; LB medium containing tryptone, yeast extract, sodium chloride, and sodium hydroxide, NZC broth containing NZ amine A (Hunko Sheffield), sodium chloride, magnesium chloride and Casamino acids (Difco); Superbroth containing tryptone, yeast extract, sodium chloride, and sodium hydroxide; tryptone broth containing tryptone and sodium chloride; TY medium containing tryptone, yeast extract, and sodium chloride; and TYGPN medium containing tryptone, yeast extract, glycerol disodium phosphate and potassium nitrate. LB medium is employed in one embodiment.

After growth of the cultures, the *E. coli* cells are typically lysed using osmotic shock, sonication or other standard means, and the expressed apoA1 is isolated from the soluble fraction. Any protein purification method may be employed for this purpose, such as dialysis, gel filtration, ion exchange chromatography, affinity chromatography, electrophoresis, or a combination of steps. In preferred embodiments employing a stretch of histidines as a tag on the expressed protein, the soluble fraction obtained after centrifugation or decantation of the aqueous layer from the cell debris is subjected to a one-step purification procedure using metal chelation chromatography. A nickel (II)-nitrilotriacetic acid agarose or a metal chelating Sepharose® column charged with nickel (II) are employed in some embodiments.

It is an advantage of the invention that T7 RNA polymerase synthesizes RNA at a rate several times that of $E.$ $coli$ RNA polymerase and terminates transcription less frequently. Moreover, T7 RNA polymerase is highly selective for initiation of its own promoter sequences and does not initiate transcription from $E.$ $coli$ DNA sequences. In addition, T7 RNA polymerase is resistant to many antibiotics such as rifampicin that inhibit $E.$ $coli$ RNA polymerase, so that expression of genes under control of a T7 RNA polymerase promoter can be maximized.

It is another advantage of the invention that, under optimal conditions, extraordinarily high yields of expressed protein can be achieved. For example, in the practice of the invention, apolipoprotein A1 accumulates to greater than 25% of the total bacterial protein in the culture, and yields of about 30 to 40% are described in the Examples hereinafter. In comparison to expression of other proteins using similar T7 RNA polymerase/promoter system, yields are unexpectedly high in both small-scale benchtop cultures and large, commercial fermentors. Preferred embodiments produce yields of at least 1 mg apoA1 per liter of culture, preferably about 2 to 3, and yields as high as from about 5 to about 8 mg protein per liter of culture, are achieved in especially preferred embodiments.

It is a further advantage of the invention that the system can be manipulated so that proteins that are easily purified can be expressed. In preferred embodiments of the invention, for example, vectors expressed as fusion products with a stretch of histidine residues at the amino terminus yield mature, stable, and biologically active apoA1 proteins that can be purified to homogeneity in simple, one-step affinity chromatography procedure. Economical production of apoA1 is thus achieved on a large scale.

The following examples are presented to further illustrate and explain the present invention and should not be taken as limiting in any regard.

EXAMPLES

Example 1

ApoA1 cDNA is subcloned in a T4 expression vector in this example.

A segment of apoA1 cDNA encoding mature apoA1 is subcloned into pET11d-6His (Hoffman, A., and Roeder, R. G., $Nucl.$ $Acids$ $Res.$ 19: 6337–6338 (1991)). In this vector, proteins are expressed under T7 control as fusion products with a stretch, at the amino terminus, of six histidine residues (for ease in subsequent purification, by elution from nickel chelating resins). Briefly stated, tags containing 6 histidines are inserted between the NcoI and BamHI sites of the bacterial expression vector pET11d obtained from Novagen, Madison, Wis.

To introduce apoA1 cDNA into this vector, a polymerase chain reaction (PCR) product encompassing the mature segment of apoA1 is synthesized using the following synthetic primers:

(SEQ ID NO 1)
AGCCGAGGATC CCTCACTGGG TGTTGAGCTT (SEQ ID NO 2)
CTTTCGCATA TGGATGAACC CCCCCAGAGC

These primers introduce BamH1 and Nde1 restriction sites at the 3' and 5' ends, respectively, of the PCR product.

The template for the PCR amplification is pA1-101 (Karathanasis, et al., cited above), a plasmid vector bearing an apoA1 cDNA which includes all the sequences for the mature apoA1 (Cheung and Chan, cited above). Briefly stated, apoA1 double-stranded cDNA clones of various lengths are isolated by screening an adult human liver cDNA library. Large scale growths of clones are carried out in 250 ml of 1% NZ-amine (an enzymatic digest of casein, Humko, Norwich, N.Y.)/0.5% yeast extract/0.01% casamino acid/10 mM $MgSO_4$ broth with $E.$ $coli$ strain LE392 used as host. Recombinant phage is precipitated with polyethylene glycol and purified on CsCl step gradients. Mapping using conventional digestion with restriction enzymes followed electrophoresis shows that the insert of clone pAI-101 contains the entire 3' untranslated region and part of the poly(A) tail of apo A-I mRNA.

Conditions for the PCR are those recommended by the vendor, Perkin Elmer, Norwalk, Conn. The 30-cycle amplification includes the following steps: 94° C., 1 minute; 55° C., 2 minutes; 72° C., 2 minutes. The PCR product is authenticated by its size (ca. 950 base pairs) as determined by electrophoresis in 1% agarose gel and the presence of appropriate SacI and StuI restriction sites predicted by the sequence set out in Karathanasis, et al., cited above.

The NdeI- and BamHI-cleaved PCR product is ligated into pET11d-6His vector restricted at the same sites. The resulting recombinant plasmid, designated pET-His.A1, is transformed into competent $E.$ $coli$ DH5α (GIBCO-BRL, Grand Island, N.Y.). Resistant to antibiotics, they yield resistant transformants at high efficiency when exposed to plasmids carrying antibiotic resistant genes. The resulting recombinant clones are screened for the presence of PCR product by colony hybridization employing $^{32}P$-end-labelled primer SEQ ID NO 1 set out above as a probe. Isolated plasmid DNA from clones testing positive are analyzed by restriction digestion with NdeI and BamHI. A plasmid liberating the 950 base pair PCR product is selected for transformation of BL21(DE3)pLysS $E.$ $coli$ (Novagen, Madison, Wis.) for final expression of recombinant apoA1. The $E.$ $coli$ strain containing the plasmid was deposited in the American Type Culture Collection (A.T.C.C.), 12301 Parklawn Drive, Rockville, Md. 20852, U.S.A., and bears accession number A.T.C.C. 69581.

Example 2

ApoA1 is expressed in bacteria in this example.

After transformation with pET-6His.A1 prepared in Example 1 above, 1 ml cultures of BL21(DE3)pLysS $E.$ $coli$ in LB media containing 10 g tryptone, 5 g yeast extract, 5 g NaCl, and 1 ml 1N NaOH per liter. When an optical density (O.D.) at 595 nm of 0.3 is reached, the cells are induced with 2 mM isopropylthiogalactose (IPTG) for 3 hours. Total cell lysates obtained by resuspending cells in 100 µl Laemmli sample buffer (1% sodium dodecyl sulfate, SDS), sonicating for 30 seconds at a sonicator setting of 6, and boiling for 10 minutes are analyzed on SDS-PAGE. Induced cell extracts are found to contain recombinant apoA1 at levels of 30% to 40% of the total bacterial protein. The identity of recombinant apoA1 in extracts are established by the appearance of a band with the expected molecular weight of about 28 kiloDaltons only upon IPTG induction and the reactivity of this band with anti-apoA1 antibodies (Sigma, St. Louis, Mo.) upon Western blotting.

To purify recombinant apoA1 on a pilot scale, a liter culture of PL21(DE3)pLysS E. coli harboring pET-6His.A1 is grown to an O.D. of 0.3 at 37° C. and then induced with 2 mM IPTG for 3 hours at 30° C. After harvesting by centrifugation, the cells are lysed by suspending them at 4° C. in 20 mM Tris.HCl, pH 7.9 buffer containing 10% glycerol, 0.2 mM EDTA, 2 mM dithiothreitol, 0.1 mM phenylmethylsulfonyl fluoride, 0.5M KCl, and pepstatin and antipain each at 20 µg/ml, making the suspension 0.1% with Nonidet P-40®, holding for 10 minutes on ice, and sonicating briefly.

Upon fractionation of total cell extracts into soluble and membrane fractions by centrifugation and analysis on SDS-PAGE (polyacrylamide gel electrophoresis), about 40% of apoA1 is in the soluble fraction. ApoA1 is purified from this fraction by a one-step affinity chromatography on a $Ni^{2+}$-NTA agarose column (Qiagen, Studio City, Calif.). The protein is adsorbed onto about 2 ml of $Ni^{2+}$-NTA agarose by a batch method for 1 hour at 4° C. After extensive washing with 20 mM imidazole in lysis buffer (25 mM Tris, pH 8.0 and 0.5M NaCl), the final elution is achieved with 100 mM imidazole in lysis buffer. Near homogeneous preparations of recombinant apoA1 are obtained with a total yield from the soluble fraction corresponding to 8 mg of pure protein per liter of bacterial culture.

Example 3

In this example, apoA1 is expressed on a large scale by growing BL21(DE3)pLysS E. coli harboring pET-6His.A1 in 10-liter fermentors. Bacteria are grown at 30° C. with agitation of 300 rpm in modified M9 media containing $Na_2HPO_4$, $KH_2PO_4$, $NH_4Cl$, NaCl, and $CaCl_2$ supplemented with casaminoacids, glucose and ampicillin (0.1 mg/ml). Cells are induced with IPTG at an optical density (O.D.) of 20 and harvested when they reached O.D. 35.

Up to 1.5 grams of highly purified apoA1 (at about 5 mg/ml) from each fermentor are then obtained by chromatography of bacterial extracts on metal-chelating Sepharose columns (Pharmacia LKB, Piscataway, N.J.) charged with $Ni^{2+}$. Frozen cells from 9 liters of culture are homogenized in 1 liter of lysis buffer. The extract is centrifuged to remove the cell debris and the resulting supernatant (1.5 l) is adsorbed overnight onto 400 ml of the nickel-charged resin. The resin is extensively washed batchwise, first with the lysis buffer and then with 5 mM imidazole in the same buffer. The resin is then packed into a column and washed with several column volumes of 25 mM imidazole in lysis buffer. The bound protein is finally slowly eluted with 0.1M EDTA in lysis buffer.

Example 4

This example compares and contrasts the protein yields of apoA1 obtained using the T7 RNA polymerase/promoter system described in Examples 2 and 3 above with yields of different proteins obtained using similar systems.

Transcription factor TFIIB, a factor required by RNA polymerase II for accurate transcription initiation through eukaryotic core promoter elements, is expressed in the bacterial system by introducing an NdeI restriction site into plasmid pB3 containing TFIIB, subcloning the mutagenized cDNA into 6His-pET11d to obtain pIIB-6His, and transforming into E. coli BL21(DE3)pLysS as described by Malik, et al., Proc. Natl. Acad. Sci. 88: 9553-9557 (1991). Yields of about 100 µg/l culture are obtained using the bacterial expression system, representing a significant improvement over isolation from eukaryotic cells (ibid.), but much less than the milligram quantities of apoA1 obtained in the practice of the invention.

Yields obtained using the method of the invention are also considerably greater than those previously reported by other investigators. For example, Citovsky, et al., reported a yield of only 100 to 200 µg Agrobacterium VirE2 protein/$10^9$ cells (and lost 50% of the yield in a presolubilization step, Citovsky, V., et al., Proc. Nat. Acad. Sci. 86: 1193-1197 (1989)). In the expression of $\beta_2$ adrenergic receptor, Breyer, et al., achieved an expression level of only 0.01% of the total protein (Breyer, R. M., et al., EMBO J. 9: 2679-2684 (1990)). In a preparation of recombinant cytochrome C reductase, Campbell obtained 0.172 mg/ml protein in the crude extract (and had to purify using a monoclonal antibody-based immunoaffinity chromatography, Campbell, W. H., Plant Physiol. 99: 693-699 (1992)).

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention as defined in the appended claims. The claims are meant to cover the claimed components and steps in any sequence which is effective to meet the objectives there intended, unless the context specifically indicates the contrary.

BIBLIOGRAPHY

Ausubel, F. M., et al., eds., Short Protocols in Molecular Biology, 2nd ed., John Wiley & Sons, New York, 1992, Figure 16.2.1, page 16-7.
Breyer, R. M., et al., EMBO J. 9: 2679-2684 (1990).
Campbell, W. H., Plant Physiol. 99: 693-699 (1992).
Cheung, P., and Chan, L., Nucl. Acids Res. 11: 3703-3715 (1983).
Citovsky, V., et al., Proc. Nat. Acad. Sci. 86: 1193-1197 (1989).
Flegel, W. A., et al., Infection and Immunity 61: 5140-5146 (1993).
Hoffman, A., and Roeder, R. G., Nucl. Acids Res. 19: 6337-6338 (1991).
Karathanasis, S., et al., Proc. Natl. Acad. Sci. USA 80: 6147-6151 (1983).
Malik, S., et al., Proc. Natl. Acad. Sci. 88: 9553-9557 (1991).
Mallory, J. B., et al., J. Biol. Chem. 262: 4241-4247 (1987).
Studier, F. W., and Moffatt, B. A., J. Mol. Biol. 189: 113-130 (1986).

We claim:

1. A method for the preparation of biologically active apolipoprotein A1, said method comprising:
   (a) subcloning apolipoprotein A1 cDNA into an *Escherichia coli* plasmid to obtain a recombinant apoA1 fusion protein-encoding plasmid, wherein said cDNA is operatively linked to a bacteriophage T7 RNA polymerase promoter and encodes an apolipoprotein A1 fusion protein that comprises an apolipoprotein A1 polypeptide fused in frame to an amino acid sequence that facilitates purification;
   (b) transferring said recombinant plasmid to an *Escherichia coli* strain containing inducible bacteriophage T7 RNA polymerase, to yield a transformed strain;
   (c) inducing said T7 RNA polymerase in said transformed strain and growing said transformed strain in a culture for a sufficient time and under appropriate conditions to produce said apolipoprotein A1 fusion protein;
   (d) lysing transformed cells harvested from said culture;
   (e) obtaining a soluble fraction from said lysed cells; and
   (f) isolating said apolipoprotein A1 fusion protein from said soluble fraction by one-step chromatography of said fraction.

2. A method according to claim 1 wherein the *E. coli* plasmid containing a bacteriophage T7 RNA polymerase promoter is a pT or pET plasmid.

3. A method according to claim 2 wherein the *E. coli* plasmid is a pET plasmid selected from the group consisting of pET3, pET5, pET9, pET11, pET12, pET14, pET15, pET16, pET17, and pET19 to pET 25 plasmids.

4. A method according to claim 3 wherein the *E. coli* plasmid is a pET11d plasmid.

5. A method according to claim 1 wherein the *E. coli* strain containing inducible bacteriophage T7 RNA polymerase is a BL21(DE3) or HMS174(DE3) strain.

6. A method according to claim 1 which yields at least about 2 to 3 milligrams apolipoprotein A1 per liter of culture.

7. A method according to claim 10 wherein the *Escherichia coli* plasmid containing a bacteriophage T7 RNA polymerase promoter and a DNA sequence encoding an amino acid sequence that facilitates purification of expressed proteins is pET11d-6His.

8. A method according to claim 1 wherein wherein the *Escherichia coli* strain containing inducible bacteriophage T7 RNA polymerase is BL21(DE3)pLysS.

9. A method according to claim 8 wherein protein expression is induced by adding isopropylthiogalactose to the culture.

10. A method according to claim 1 wherein the amino acid sequence that facilitates purification of expressed proteins comprises a cluster of histidine residues.

11. A method according to claim 1 wherein one-step chromatography is accomplished using a Ni(II) affinity or chelating column.

12. A method according to claim 1 wherein the chromatography step comprises using a nickel(II)-nitrilotriacetic acid agarose column.

13. A method according to claim 6 wherein at least about 5 to 8 milligrams apolipoprotein A1 are obtained per liter of *Escherichia coli* culture.

14. A method for the preparation of biologically active human apolipoprotein A1 in high yield comprising:

(a) subcloning apolipoprotein A1 cDNA into *Escherichia coli* plasmid pET11d-6His to obtain a recombinant apolipoprotein A1 fusion protein-encoding plasmid, wherein said cDNA is operatively linked to a bacteriophage T7 RNA polymerase promoter and encodes an apolipoprotein A1 fusion protein that comprises an apolipoprotein A1 polypeptide containing six additional histidine residues at its aminoterminus;

(b) transferring said recombinant plasmid to *Escherichia coli* strain BL21(DE3)pLysS to yield a transformed strain;

(c) inducing said T7 RNA polymerase in said transformed strain by adding isopropylthiogalactose and growing said transformed strain in a culture for a sufficient time and under appropriate conditions to produce said fusion protein;

(d) obtaining a soluble fraction from the culture after lysing the cells; and (e) isolating the apolipoprotein A1 fusion protein in yields of at least about 1 mg/l culture by chromatography of the fraction obtained in step (d) on a nickel (II) affinity or chelating column.

15. A method according to claim 14 wherein the column is a nickel (II)-nitrotriacetic acid agarose column.

* * * * *